(12) United States Patent  (10) Patent No.: US 7,183,117 B2
Fukuizumi et al.  (45) Date of Patent: Feb. 27, 2007

(54) APPARATUS FOR MEASURING CHARACTERISTICS OF CHEMICAL SOLUTION, CHEMICAL SOLUTION SUPPLY APPARATUS, AND METHOD FOR MEASURING CONCENTRATION OF CHEMICAL SOLUTION

(75) Inventors: Masataka Fukuizumi, Kasugai (JP); Hiroshi Osuda, Kasugai (JP); Toru Matoba, Kasugai (JP); Takeshi Nakamura, Kasugai (JP)

(73) Assignee: Fujitsu Limited, Kawasaki (JP)

( * ) Notice: Subject to any disclaimer, the term of this patent is extended or adjusted under 35 U.S.C. 154(b) by 524 days.

(21) Appl. No.: 10/277,158

(22) Filed: Oct. 22, 2002

(65) Prior Publication Data

US 2003/0119198 A1 Jun. 26, 2003

(30) Foreign Application Priority Data

Dec. 20, 2001 (JP) ............................. 2001-387611

(51) Int. Cl.
*G01N 27/416* (2006.01)
*G01N 27/04* (2006.01)

(52) U.S. Cl. ............... 436/150; 422/62; 422/82.01; 422/82.02; 436/52; 436/100; 436/149; 436/151

(58) Field of Classification Search .............. 422/62, 422/81, 82.01–82.02; 436/52, 100, 149–151
See application file for complete search history.

(56) References Cited

U.S. PATENT DOCUMENTS 4,145,923 A * 3/1979 McClure .................. 73/861.05
4,193,291 A * 3/1980 Lynnworth .................. 73/32 A
4,275,448 A * 6/1981 Le Dall ....................... 700/271
4,823,987 A * 4/1989 Switall .......................... 222/63
5,522,660 A * 6/1996 O'Dougherty et al. ....... 366/136
5,670,376 A * 9/1997 Obeng .......................... 436/55
5,708,191 A * 1/1998 Greenwood et al. ......... 73/32 A
5,741,962 A * 4/1998 Birchak et al. ........... 73/152.16
5,924,794 A  7/1999 O'Dougherty et al.
5,945,830 A * 8/1999 Magowan et al. ........... 324/438
6,086,753 A * 7/2000 Ericson et al. .............. 210/120
6,721,628 B1* 4/2004 Lai et al. ..................... 700/266

FOREIGN PATENT DOCUMENTS

JP  63-311166  12/1988
JP  05-026853  2/1993

(Continued)

OTHER PUBLICATIONS

Norlin, P et al, Sensors and Actuators B 1998, 49, 34-39.*

(Continued)

*Primary Examiner*—Arlen Soderquist
(74) *Attorney, Agent, or Firm*—Armstrong, Kratz, Quintos, Hanson & Brooks, LLP

(57) ABSTRACT

A supply apparatus for preparing a mixed chemical solution of a predetermined mixing ratio at a low cost and for supplying the mixed chemical solution stably. The supply apparatus includes a measuring apparatus located on an intermediate portion of a flow channel through which the chemical solution flows upward for measuring properties of the mixed chemical solution. In the lower portion of the measuring apparatus, disposed is a nozzle for spouting the chemical solution upward.

11 Claims, 3 Drawing Sheets

FOREIGN PATENT DOCUMENTS

| | | | |
|---|---|---|---|
| JP | 6-37080 | * | 2/1994 |
| JP | 08-021825 | | 1/1996 |
| JP | 8-159946 | * | 6/1996 |
| JP | 9-129588 | * | 5/1997 |
| JP | 63-38466 | | 2/1998 |
| JP | 11-500846 | | 1/1999 |
| JP | 11-211705 | * | 8/1999 |
| JP | 2000-313978 | * | 11/2000 |
| JP | 2000-313979 | * | 11/2000 |
| JP | 2001-179063 | * | 7/2001 |

OTHER PUBLICATIONS

Andrade, F. J. et al, Analytica Chimica Acta 1999, 379, 99-106.*
Nomura, T. et al, Sensors and Actuators B 2001, 76, 69-73.*
Voloudakis, K. et al, Measurement Science and Technology 1999, 10, 100-105.☐☐.*

* cited by examiner

APPARATUS FOR MEASURING CHARACTERISTICS OF CHEMICAL SOLUTION, CHEMICAL SOLUTION SUPPLY APPARATUS, AND METHOD FOR MEASURING CONCENTRATION OF CHEMICAL SOLUTION

BACKGROUND OF THE INVENTION

The present invention relates to an apparatus for supplying a chemical solution to a manufacturing apparatus of an electronic device, such as a semiconductor device and an LCD device. More particularly, the present invention relates to an apparatus for supplying a mixed chemical solution having a predetermined concentration prepared by mixing a plurality of stock chemical solutions.

In a manufacturing process of electronic devices, many kinds of chemical solutions are used in large quantities. Specifically, a diluted chemical solution and/or a mixed chemical solution prepared by mixing a plurality of stock chemical solutions at predetermined concentrations are used in large quantities.

The mixed chemical solution is prepared by a chemical solution supply apparatus. The chemical solution supply apparatus has a conductivity meter for measuring the electrical conductivity, a sonic speedometer for measuring sonic velocity (propagation velocity of a sonic wave in the chemical solution), and a thermometer for measuring temperature of the chemical solution. The chemical solution supply apparatus measures the concentration of the mixed chemical solution by comparing the measured values of the electrical conductivity, the sonic velocity and the temperature with the calibration curves prepared beforehand. The chemical solution supply apparatus adjusts the mixture ratio of a plurality of stock chemical solutions so that the measured concentration may be equal to a predetermined value, and supplies the mixed chemical solution maintained at the predetermined concentration to a device manufacturing apparatus.

Furthermore, a mixed chemical solution regulated to the predetermined concentration beforehand may be purchased from a chemical solution maker, and may be supplied to the device manufacturing apparatus.

However, when the chemical solution supply apparatus stirs a mixed chemical solution, bubbles are generated in the mixed chemical solution, and the bubbles adhere to the conductivity meter, the sonic speedometer and the thermometer. The measured values vary owing to the stuck bubbles, so that the electrical conductivity, the sonic velocity and the temperature cannot accurately be measured, which makes it difficult to maintain the concentration of the mixed chemical solution at the desired concentration. As a result, the concentration of the mixed chemical solution supplied to the device manufacturing apparatus varies, so that defects easily occur in semiconductor devices manufactured by the device manufacturing apparatus.

In order to accurately measure the concentration of a mixed chemical solution, it has been suggested that an automatic neutralization titration apparatus in which neutralization titration is automatically carried out be incorporated into the chemical solution supply apparatus. However, since the neutralization titration analysis takes about ten minutes at the shortest for one analytical operation, even the automatic neutralization titration apparatus cannot monitor the concentration of a mixed chemical solution throughout.

Furthermore, it is necessary to replenish the reagents required for the neutralization titration analysis, and the shorter is the interval between the neutralization titration analysis operations, the shorter is the replenishment interval of the reagents. In consequence, the replenishment operation becomes complicated. In addition, a drainage treatment for purifying the waste liquid generated by the neutralization titration analysis is also required.

On the other hand, when a mixed chemical solution adjusted to the predetermined concentration is purchased from a chemical solution maker, a unit price of the chemical solution is higher than that of a single component chemical solution. Moreover, the time period between the manufacture of the chemical solution by the chemical solution maker and the supply of the chemical solution to the device manufacturing apparatus is long, and hence, it is difficult to maintain the concentration of the mixed chemical solution.

SUMMARY OF THE INVENTION

An object of the present invention is to provide a chemical solution supply apparatus by which a mixed chemical solution having a predetermined concentration can be stably supplied at a low cost.

To achieve the above object, the present invention provides an apparatus for measuring a property of a chemical solution, located on an intermediate portion of a flow channel through which the chemical solution flows upward The apparatus has a nozzle arranged at the lower portion of the measuring apparatus, for spouting the chemical solution upward in the measuring apparatus.

A further perspective of the present invention is a chemical solution supply apparatus for supplying a mixed chemical solution of a plurality of stock solutions to an external circuit. The supply apparatus includes a mixing tank for mixing the plurality of stock solutions supplied from a plurality of stock chemical solution supply sources, respectively, a circulation pipe which is connected to the mixing tank at both ends thereof and through which the mixed chemical solution flows. The circulation pipe has a portion through which the mixed chemical solution flows upward. A circulation pump is located on the portion of the circulation pipe and circulates the mixed chemical solution through the circulation pipe. A supply pipe is connected to the mixing tank and has a delivery pump for supplying the mixed chemical solution from the mixing tank to the external circuit. A measuring apparatus arranged at the portion of the circulation pipe measures a concentration of the mixed chemical solution. The measuring apparatus has an upper portion and a lower portion connected with the circulation pump, and a nozzle arranged on the lower portion of the measuring apparatus and communicated to the circulation pipe. The mixed chemical solution is spouted upward from the nozzle. A controller controls mixing of the plurality of stock solutions and supply of the mixed chemical solution. The controller adjusts a concentration of the mixed chemical solution on the basis of the results measured by the measuring apparatus.

A further perspective of the present invention is a method of measuring a concentration of a chemical solution. The method includes making a calibration curve for the concentration of the chemical solution by the use of an electrical conductivity of the chemical solution, a propagation velocity of sonic wave in the chemical solution and a temperature of the chemical solution as parameters, measuring the electrical conductivity of the chemical solution, the propagation velocity of the sonic wave in the chemical solution, and the temperature of the chemical solution, and calculating the concentration of the chemical solution based on the results of the measuring step and the calibration curve.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF PREFERRED EMBODIMENTS

Figure 1:
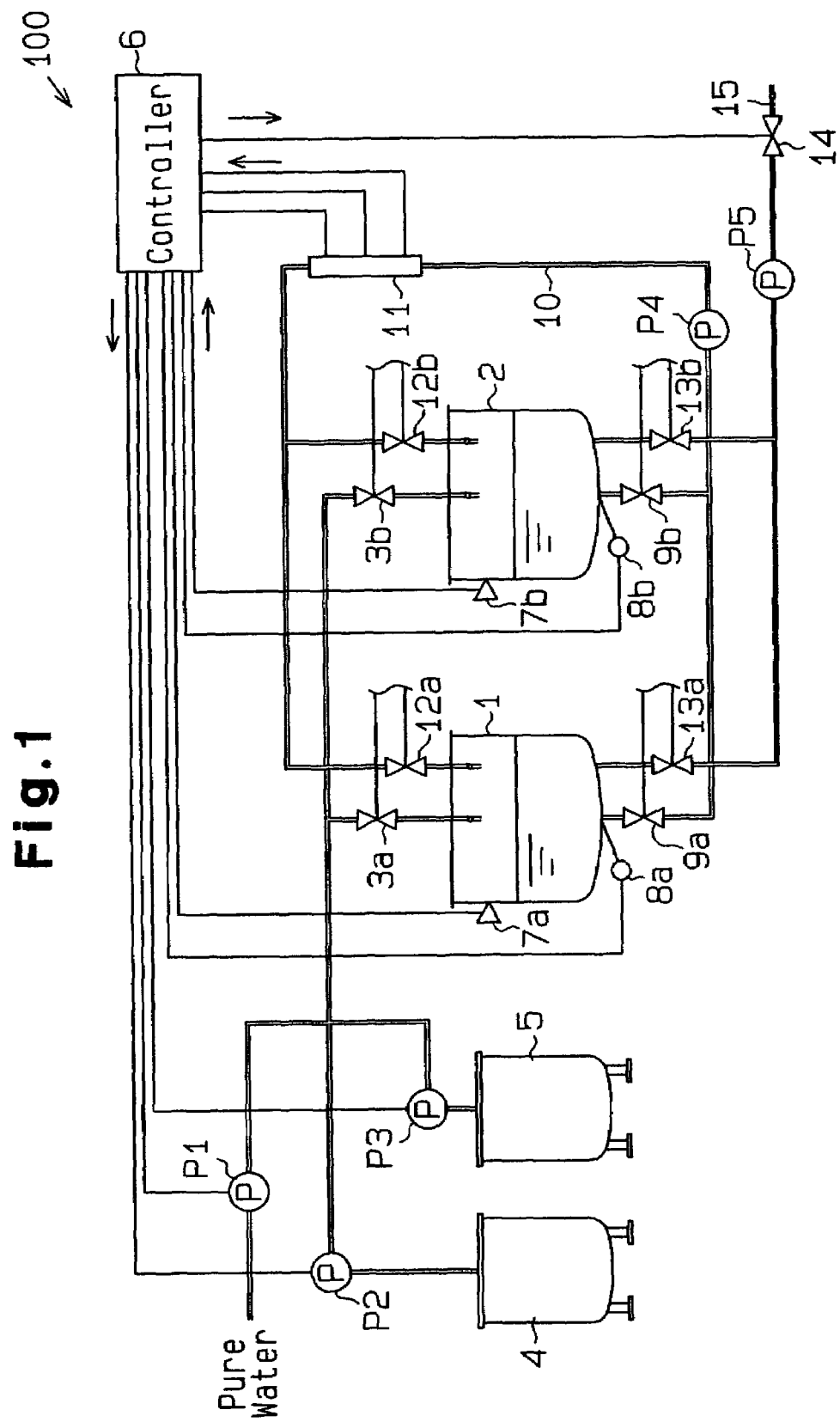
FIG. 1 is a schematic view of one embodiment of a chemical solution supply apparatus according to the present invention.

FIG. 1 is a schematic diagram of one embodiment of a chemical solution supply apparatus 100 according to the present invention. The chemical solution supply apparatus 100 has a first mixing tank 1 and a second mixing tank 2. While a chemical solution is supplied from one tank to a device manufacturing apparatus not shown in the drawings, preparation (mixing) of the chemical solution is carried out in the other tank. Thus, a fresh chemical solution is prepared in the mixing tanks 1 and 2 alternately, and the chemical solution supply apparatus 100 can supply continuously a fresh chemical solution from the mixing tanks 1 and 2.

Pure water is supplied via a pure water pump P1 and valves 3a, 3b to the first and second mixing tanks 1, 2, respectively. The chemical solution supply apparatus 100 has a first stock chemical solution tank 4 and a second stock chemical solution tank 5. The first stock chemical solution tank 4 stores a first stock chemical solution, or ammonium fluoride ($NH_4F$). The ammonium fluoride is supplied via a second pump P2 and valves 3a, 3b to the first and the second tanks 1, 2, respectively. The second stock chemical solution tank 5 stores a second stock chemical solution, or hydrofluoric acid (HF). The hydrofluoric acid is supplied from the second stock chemical solution tank 5 via a third pump P3 and valves 3a, 3b to the first and the second tanks 1, 2, respectively.

The pumps P1 to P3 and the valves 3a, 3b are connected to a controller 6. The pumps P1 to P3 operate according to the control signals output from the controller 6, and the valves 3a, 3b are opened and closed on the basis of the control signals output from the controller 6.

Stirrers (not shown) for stirring the chemical solution in each mixing tank 1, 2 are disposed in the first and the second mixing tanks 1, 2. Within the first and the second mixing tanks 1, 2, formed is buffered HF by mixing the pure water, the ammonium fluoride and the fluoric acid.

On the first and the second tanks 1, 2, disposed are level meters 7a, 7b for measuring the volumes of the chemical solution in the first and the second tanks 1, 2. Each of the level meters 7a, 7b outputs measured volumes to the controller 6.

On the first and the second tanks 1, 2, disposed are weight scales 8a, 8b for measuring the weights of the chemical solution in the first and the second tanks 1, 2. Each of the weight scales 8a, 8b outputs the measured weights to the controller 6.

When mixing the chemical solution in each of the tanks 1, 2, the controller 6 controls the pumps P1 to P3 and the valves 3a, 3b to supply pure water, ammonium fluoride and fluoric acid, in this order, to each mixing tank 1, 2.

The volumes and weights of the chemical solution in each of the mixing tanks 1, 2 are measured with the level meters 7a, 7b and the weight scales 8a, 8b. The controller 6 preliminary calculates rough concentrations (concentration of each component) of the chemical solution in the mixing tanks 1, 2 on the basis of the measured volumes and weights.

That is, since each stock chemical solution is supplied in order into each of the mixing tanks 1, 2, the controller 6 can catch the volume and weight of each stock chemical solution. The controller 6 calculates ratio (composition) of each stock chemical solution (component) in the mixed chemical solution on the basis of the volume and weight of each stock chemical solution. After charging of each stock chemical solution is finished, the controller 6 calculates rough concentration of the mixed chemical solution in each of the mixing tanks 1, 2 on the basis of the volume and weight of each stock chemical solution.

The mixing tank 1 is connected to a circulation pipe 10 via a valve 9a and the mixing tank 2 is connected to the circulation pipe 10 via a valve 9b.

In the circulation pipe 10 disposed are a circulation pump P4 and a concentration measuring apparatus 11, and the mixed chemical solution in each of the mixing tanks 1, 2 is guided via the circulation pipe 10 to the concentration measuring apparatus 11. The mixed chemical solution is returned into each of the mixing tanks 1, 2 via valves 12a, 12b after passing through the measuring apparatus 11.

The controller 6 controls the circulation pump P4 and the valves 9a, 9b, 12a and 12b. Once the circulation pump P4 operates and the valves 9a, 12a, are opened, the mixed chemical solution in the first mixing tank 1 is circulated via the circulation pipe 10. On the other hand, once the circulation pump P4 operates and the valves 9b, 12b, are opened, the mixed chemical solution in the second mixing tank 2 is circulated via the circulation pipe 10.

Each of the mixing tanks 1, 2 is connected to a supply pipe 15 via valves 13a, 13b. A deliver pump P15 and a supply valve 14 are disposed in the supply pipe 15.

The controller 6 controls the deliver pump P5 and the valves 13a, 13b and 14. Once the deliver pump P5 operates and the valves 13a, 14, are opened, the mixed chemical solution in the first mixing tank 1 is supplied to the device manufacturing apparatus via the supply pipe 15. On the other hand, once the circulation pump P5 operates and the valves 13b, 14, are opened, the mixed chemical solution in the second mixing tank 2 is supplied to the device manufacturing apparatus via the supply pipe 15.

Figure 2:
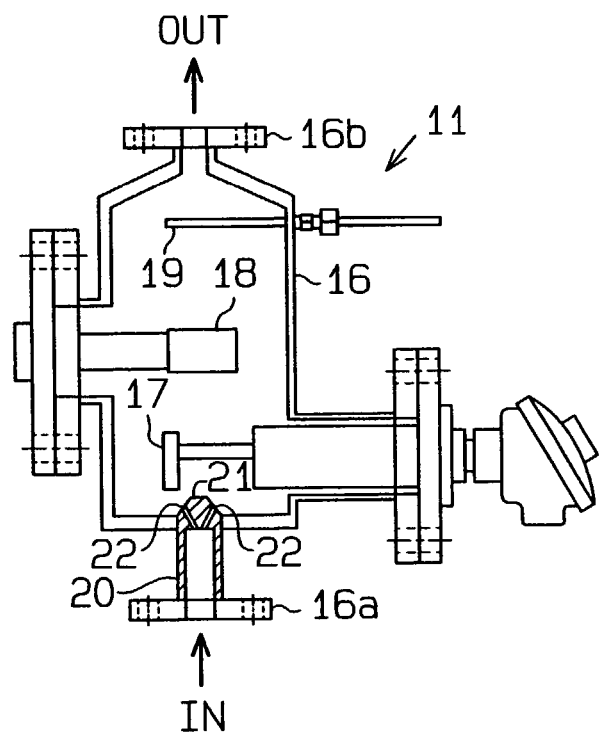
FIG. 2 is a schematic view of a concentration measuring apparatus in FIG. 1.

The concentration measuring apparatus 11 will be described according to FIG. 2. The concentration measuring apparatus 11 includes a coupling pipe 20 having a lower flange 16a to be connected to the circulation pipe 10, a measurement cylinder 16 having an upper flange 16b and detectors 17, 18 and 19 housed in the measurement cylinder 16, for detecting physical properties of the mixed chemical solution. The detectors 17, 18 and 19 include a sonic speedometer 17, a conductivity meter 18 and a thermometer 19 arranged in this order from the lower portion in the measurement cylinder 16. The mixed chemical solution is supplied into the measurement cylinder 16 from the lower flange 16a side and is exhausted from the upper flange 16b side. That is, the mixed chemical solution passes through the measurement cylinder 16 from the lower portion toward the upper portion.

On the top end of the coupling pipe 20 formed is a nozzle 21. Two spout holes 22, which are open within the measurement cylinder 16 and 6 mm in diameter, are disposed on the nozzle 21. Each spout hole 22 extends obliquely at an angle of 25 degrees with respect to the center axis (vertical line) of the measurement cylinder 16 so as to spout the mixed chemical solution toward the inner wall of the measurement cylinder 16. The mixed chemical solution guided through the coupling pipe 20 from the circulation pipe 10 is spouted vigorously into the measurement cylinder 16 from the spout holes 22 of the nozzle 21. Thereby, bubbles included in the mixed chemical solution are blown off upward by a jet of the chemical solution itself. If there are bubbles adhering to the sonic speedometer 17, the conductivity meter 18 and the thermometer 19, the bubbles are expelled from the sonic speedometer 17, the conductivity meter 18 and the thermometer 19 by a jet of the mixed chemical solution. Therefore, adhering of the bubbles to the sonic speedometer 17, the conductivity meter 18 and the thermometer 19 is prevented. Consequently, each of the sonic velocity, the electrical conductivity and the temperature of the mixed chemical solution is measured accurately with the sonic speedometer 17, the conductivity meter 18 and the thermometer 19.

Measured signals of the sonic speedometer 17, the conductivity meter 18 and the thermometer 19 are output to the controller 6. The controller 6 calculates the concentration (composition) of the mixed chemical solution on the basis of comparison between the measured signals and the calibration curve prepared beforehand.

Figure 3:
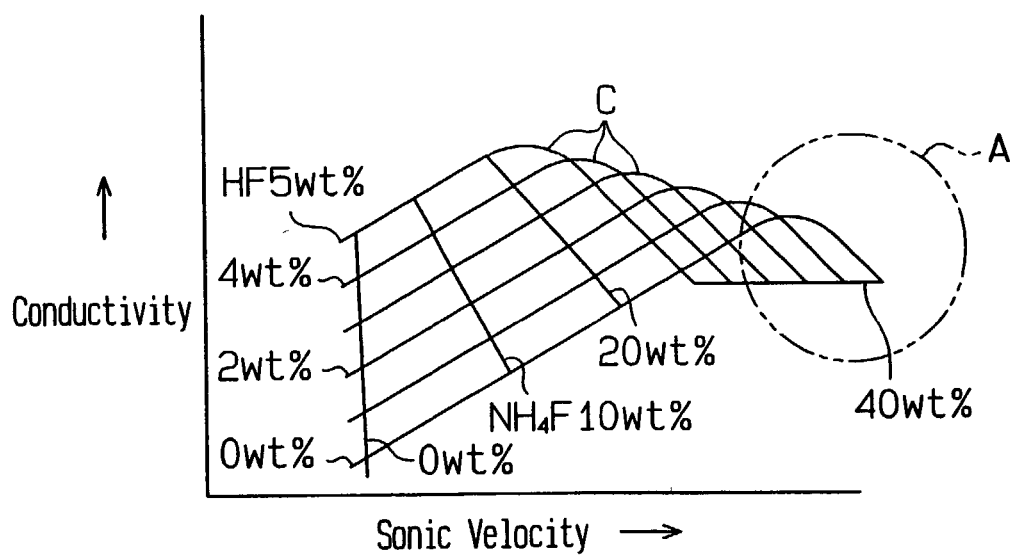
FIG. 3 is a graph showing a calibration curve for a mixed chemical solution.

FIG. 3 is a graph of the calibration curves to calculate the concentration of the mixed chemical solution from the electrical conductivity and sonic velocity of the buffered HF. Further, although the electrical conductivity and the sonic velocity vary depending on the temperature, relative relationship between the calibration curves are constant, and therefore the description of the temperature changes thereof will be omitted.

The controller 6 compares the electrical conductivity and the sonic velocity measured with the concentration measuring apparatus with the calibration curve for the desired concentration of the mixed chemical solution. The controller 6 adjusts precisely the concentration of the mixed chemical solution by adding the stock chemical solution (hydrofluoric acid and ammonium fluoride) so that the electrical conductivity and the sonic velocity may correspond with the desired location on the calibration curve.

Figure 4:
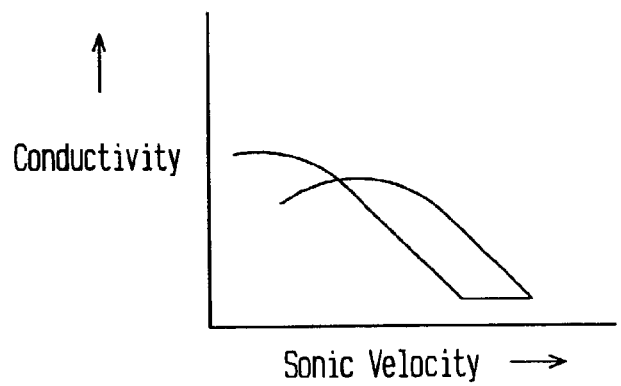
FIG. 4 is a graph showing the partial calibration curve in which an A portion in FIG. 3 is enlarged.

FIG. 4 is a graph showing a part of the calibration curves, i.e. the A portion of the calibration curves, enlarged, shown in FIG. 3. Using such calibration curves, the concentration of the mixed chemical solution is further finely and precisely adjusted.

Figure 5:
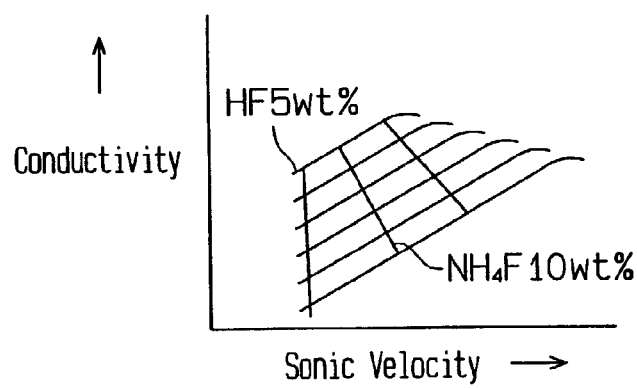
FIGS. 5 and 6 are graphs showing separate calibration curves made by separating the calibration curve in FIG. 3.
Figure 6:
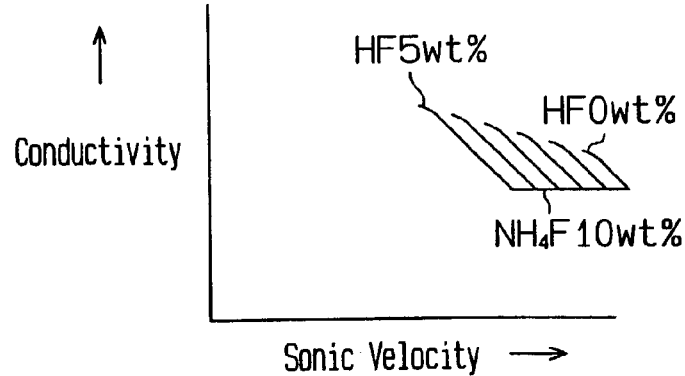

When the calibration curves have inflection points C as shown in FIG. 3, the calibration curves may be divided into a plurality of partial calibration curves as shown in FIG. 5 and FIG. 6. The controller 6 selects some partial calibration curve according to the rough concentration of the mixed chemical solution calculated from the weight and volume, and use it for fine adjustment of the concentration of the mixed chemical solution.

Next, mixing operation of a chemical solution supply apparatus 100 will be described.

The operation of preparing a buffered HF from 50 wt % hydrofluoric acid and 40 wt % ammonium fluoride will be explained. In this case, the operator inputs into the controller 6 various parameters such as concentration of each stock chemical solution, the desired concentration and volume or weight of the mixed chemical solution obtained by mixing the stock chemical solution. When the concentration of the stock chemical solution is unknown, the concentration parameter does not need to be input.

Then, in order to mix the mixed chemical solution in the first mixing tank 1, the controller 6 activates the pure water pump P1 and also opens the valve 3a to supply pure water into the first mixing tank 1. The amount of pure water supplied is calculated on the basis of the inputted concentration of the stock chemical solution and the desired concentration of the mixed chemical solution.

After a predetermined volume or weight of pure water is supplied, the controller 6 activates the second pump P2 to supply a predetermined volume or weight of ammonium fluoride from the first stock chemical solution tank 4 into the first mixing tank 1. Then, the controller 6 activates the third pump P3 to supply a predetermined volume or weight of hydrofluoric acid from the second stock chemical solution tank 5 into the first mixing tank 1.

The controller 6 calculates the concentration of the mixed chemical solution on the basis of the weights or volumes of the pure water, ammonium fluoride and hydrofluoric acid supplied into the first mixing tank 1.

The controller 6 activates the circulation pump P4 and opens the valves 9a, 12a, and stirs the mixed chemical solution in the first mixing tank 1 with the stirrer while the mixed chemical solution is being circulated via the circulation pipe 10.

The concentration measuring apparatus 11 measures the sonic velocity, the electrical conductivity and the temperature of the mixed chemical solution circulated. The controller 6 calculates the precise concentration of the mixed chemical solution using the calibration curve selected depending on the rough concentration of the mixed chemical, which has been calculated from the calibration curves set beforehand or the weight and volume thereof.

For example, when the concentration of ammonium fluoride is lower than the objective value, ammonium fluoride is added to the first mixing tank 1 and the concentration is again measured. On the other hand, when the concentration of ammonium fluoride is higher than the objective value, pure water is added to the first mixing tank 1 and the concentration is again measured. Repeating these operations, the mixed chemical solution with the desired concentration is prepared in the first mixing tank 1.

When the preparation of the mixed chemical solution is being carried out in the first mixing tank 1, supply of the mixed chemical solution into the device manufacturing apparatus is conducted in the second mixing tank 2. After the mixed chemical solution in the second mixing tank 2 is used up, the mixed chemical solution is supplied from the first mixing tank 1 into the device manufacturing apparatus. Subsequently, preparation of the mixed chemical solution is carried out in the second mixing tank 2.

The chemical solution supply apparatus 100 achieves the following advantages.

(1) In the mixing tanks 1 and 2, preparation and supply of the mixed chemical is carried out alternately. That is, while the mixed chemical solution is prepared in one mixing tank 1 (or 2), the mixed chemical solution in the other mixing tank 2 (or 1) is supplied into the device manufacturing apparatus. Thereby, the fresh mixed chemical solution is always supplied into the device manufacturing apparatus.

(2) The mixed chemical solution prepared in each mixing tank 1, 2 is guided to the concentration measuring apparatus 11. The concentration of the mixed chemical solution is measured with the concentration measuring apparatus 11. The controller 6 adjusts the concentration of the chemical solution on the basis of comparison between the measured value and the calibration curve. Therefore, prepared is the mixed chemical solution where the concentration is always maintained accurately at the desired concentration.

(3) The mixed chemical solution is spouted from the nozzle 21 into the measurement cylinder 16 in the concentration measuring apparatus. Consequently, adhering of bubbles to the sonic speedometer 17, conductivity meter 18 and thermometer 19 in the measurement cylinder 16 is prevented, and sonic velocity, electrical conductivity and temperature are measured accurately. Moreover, the mixed chemical solution is further agitated by spout through the nozzle 21 in the measurement cylinder 16. Therefore, the sonic velocity, electrical conductivity and temperature of the mixed chemical solution with homogeneous composition are measured precisely.

(4) Since the mixed chemical solution flows from the lower portion toward the upper portion in the measurement cylinder 16, the bubbles are blown off by the mixed chemical solution spouted through the nozzle 21 from the sonic speedometer 17, conductivity meter 18 and thermometer 19, and are flushed away toward the upper portion of the measurement cylinder 16.

(5) It is possible that the rough concentration of the mixed chemical solution is calculated on the basis of the volume or weight of the stock chemical solution supplied into each of the mixing tanks 1, 2, that the optimum calibration curve is selected on the basis of the rough concentration and that the accurate concentration of the mixed chemical solution is measured on the basis of the sonic velocity, electrical conductivity and temperature measured with the concentration measuring apparatus 11. Then, the concentration of the mixed chemical solution in each of the mixing tanks 1, 2 is precisely readjusted on the basis of the measured concentration.

It should be apparent to those skilled in the art that the present invention may be embodied in many other specific forms without departing from the spirit or scope of the invention. Particularly, it should be understood that the present invention may be embodied in the following forms.

The stock chemical solutions are not limited to ammonium fluoride and hydrofluoric acid, and the mixed chemical solution is not limited to buffered hydrofluoric acid.

The number of the mixing tanks 1, 2 can be any numbers except 2.

The circulation pipe 10 including the concentration measuring apparatus 11 may be disposed independently in each of the mixing tanks 1, 2.

Pure water, ammonium fluoride, and hydrofluoric acid may be pressure-fed into the first or the second mixing tank 1, 2 using an inert gas such as nitrogen except the pumps P1–P3.

The inclination angles of a plurality of spout holes 22 may be different from one another.

The present examples and embodiments are to be considered as illustrative and not restrictive, and the invention is not to be limited to the details given herein, but may be modified within the scope and equivalence of the appended claims.

What is claimed is:

1. An apparatus for measuring a property of a chemical solution, located on an intermediate portion of a flow channel through which the chemical solution flows upward, comprising:
    an upright measurement cylinder having a bottom for the inlet of the chemical solution and a top including an exhaustion port for the exhaustion of the chemical solution, wherein the measurement cylinder is configured to be located on the intermediate portion of the flow channel so that the chemical solution flows upward in the measurement cylinder and is exhausted from the measurement cylinder through the exhaustion port;
    a nozzle arranged at the bottom of the measurement cylinder for spouting the chemical solution obliquely upward to an inner wall of the measurement cylinder; and
    a detector, located above the nozzle in the interior of the measurement cylinder, for detecting the property of the chemical solution.

2. The measuring apparatus according to claim 1, wherein the nozzle is arranged in the center of the bottom of the measurement cylinder, and the nozzle has spout holes for spouting the chemical solution obliquely upward to an inner wall of the measurement cylinder.

3. A chemical solution supply apparatus for supplying a mixed chemical solution of a plurality of stock solutions to an external circuit, comprising:
    a mixing tank for mixing the plurality of stock solutions supplied from a plurality of stock chemical solution supply sources, respectively;
    a circulation pipe which is connected to the mixing tank at both ends thereof and through which the mixed chemical solution flows, the circulation pipe having a portion through which the mixed chemical solution flows upward;
    a circulation pump located on an intermediate portion of the circulation pipe, for circulating the mixed chemical solution through the circulation pipe;
    a supply pipe connected to the mixing tank and having a delivery pump for supplying the mixed chemical solution from the mixing tank to the external circuit;
    a measuring apparatus arranged at the portion of the circulation pipe, for measuring a concentration of the mixed chemical solution, the measuring apparatus including:
    an upright measurement cylinder having a bottom for the inlet of the chemical solution and a top including an exhaustion port for the exhaustion of the chemical solution, wherein the measurement cylinder is configured to be located on the intermediate portion of the flow channel so that the chemical solution flows upward in the measurement cylinder and is exhausted from the measurement cylinder through the exhaustion port;
    a nozzle, arranged at the bottom of the measurement cylinder and communicated with the circulation pump, for spouting the chemical solution obliquely upward to an inner wall of the measurement cylinder; and
    a detector, located above the nozzle in the interior of the measurement cylinder, for detecting the property of the chemical solution; and
    a controller for controlling mixing of the plurality of stock solutions and supply of the mixed chemical solution/ wherein the controller adjusts a concentration of the mixed chemical solution on the basis of the results measured by the measuring apparatus.

4. The chemical solution supply apparatus according to claim 3, wherein the nozzle is arranged in the center of the bottom portion of the measurement cylinder, the nozzle having spout holes for spouting the chemical solution obliquely to toward the inner wall of the measurement cylinder.

5. The apparatus according to claim 4, wherein the spout holes are formed to be inclined at a mutually different angle with respect to the center axis of the measurement cylinder.

6. The apparatus according to claim 4, wherein the detector is one of a plurality of detectors including a conductivity meter for measuring an electrical conductivity of the mixed chemical solution, a sonic speedometer for measuring a propagation velocity of sonic wave in the mixed chemical solution and a thermometer for measuring a temperature of the mixed chemical solution, and the controller calculates a precise concentration of the mixed chemical solution on the basis of the measured electrical conductivity, propagation velocity and temperature.

7. The apparatus of claim 6 further comprising: a level meter, located on the mixing tank, for measuring a volume of the stock chemical solution supplied into the mixing tank; and a weight scale for measuring a weight of the stock chemical solution supplied into the mixing tank, wherein the controller preliminary calculates a rough concentration of the mixed chemical solution based on the measured volume and the weight of the stock chemical solution, calculates a precise concentration of the mixed chemical solution by the use of the measured results of the conductivity meter, the sonic speedometer and the thermometer, a predetermined calibration curve and the rough concentration, and then adjusts the concentration of the mixed chemical solution based on the precise concentration.

8. The apparatus according to claim 4, wherein the mixing tank is one of a plurality of tanks including a first tank and a second tank, and the controller prepares the mixed chemical solution in the second tank while the mixed chemical solution in the first tank is being supplied to the external circuit.

9. A measuring apparatus for measuring mixing ratios of a plurality of components in a mixed chemical solution containing the plurality of components, the measuring apparatus comprising:

an upright measurement cylinder having a bottom for the inlet of the chemical solution and a top including an exhaustion port for the exhaustion of the chemical solution, wherein the measurement cylinder is configured to be located on an intermediate portion of a flow channel so that the mixed chemical solution flows upward in the measurement cylinder and is exhausted from the measurement cylinder through the exhaustion port;

a nozzle, arranged at the bottom of the measurement cylinder, for spouting the mixed chemical solution upward to an inner wall of the measurement cylinder and obliquely with respect to the central axis of the measurement cylinder and;

a sonic speedometer, located above the nozzle in the interior of the measurement cylinder, for measuring a propagation velocity of sonic wave in the mixed chemical solution;

a conductivity meter, located above the nozzle in the interior of the measurement cylinder, for measuring an electrical conductivity of the mixed chemical solution;

a thermometer, located above the nozzle in the interior of the measurement cylinder, for measuring a temperature of the mixed chemical solution; and a controller, connected to the sonic speedometer, the conductivity meter and the thermometer, for calculating a mixing ratio of the plurality of components in the mixed chemical solution on the basis of the measured electrical conductivity, propagation velocity and temperature.

10. The apparatus of claim 9, wherein the sonic speedometer, the conductivity meter and the thermometer are located coaxially with the central axis of the measurement cylinder.

11. A method of measuring a composition of a mixed chemical solution containing a plurality of components comprising the steps of:

making a calibration curve for a mixing ratio of the plurality of components by the use of an electrical conductivity of the mixed chemical solution, a propagation velocity of sonic wave in the mixed chemical solution and a temperature of the mixed chemical solution as parameters;

supplying the components to a mixing tank;

measuring the weight and volume of each components;

preliminary calculating a rough concentration of the respective components from the weight and volume;

measuring the electrical conductivity of the mixed chemical solution, the propagation velocity of sonic wave in the mixed chemical solution, and the temperature of the mixed chemical solution;

selecting an optimum portion of the calibration curve according to the rough concentration; and calculating the concentration of the respective components in the mixed chemical solution based on the electrical conductivity, the propagation velocity, the temperature, and the optimum portion of the calibration curve.

* * * * *